United States Patent [19]
Schoendorfer et al.

[11] Patent Number: 4,806,247
[45] Date of Patent: Feb. 21, 1989

[54] PLASMAPHERESIS SYSTEM AND METHOD

[75] Inventors: Donald W. Schoendorfer; Lee E. Hansen, both of Santa Ana, Calif.

[73] Assignee: Baxter International Inc., Deerfield, Ill.

[21] Appl. No.: 79,108

[22] Filed: Jul. 29, 1987

Related U.S. Application Data

[62] Division of Ser. No. 722,800, Apr. 12, 1985, Pat. No. 4,713,176.

[51] Int. Cl.$^4$ .............................................. B01D 13/00
[52] U.S. Cl. ............................ 210/321.18; 210/416.1; 210/360.1; 210/321.75
[58] Field of Search ............... 210/644, 645, 646, 647, 210/648, 649, 650, 651, 652, 780, 784, 195.2, 216, 217, 257.2, 297, 321.1, 321.2, 321.3, 359, 360.1, 433.2, 402, 416.1

[56] References Cited

U.S. PATENT DOCUMENTS 3,634,228  1/1972  Latham, Jr. .

FOREIGN PATENT DOCUMENTS 2410478  6/1979  France .

OTHER PUBLICATIONS

Murphy, S. et al., "Storage of Platelets at 22° C.", *Blood*, vol. 35, p. 549 (1970).
Murphy, S. and Gardner, F., "Platelet Storage at 22° C.: Role of Gas Transport Across Plastic Containers in Maintenance of Viability", *Blood*, vol. 46, p. 209 (1975).
Schlicter, S., "Preservation of Platelet Viability and Function During Storage of Concentrates", *The Blood Platelet in Transfusion Therapy*, Alan R. Liss, Inc., NY pp. 83-100 (1978).
Rock, G. and Figuerdo, A., "Metabolic Changes During Platelet Sotrage", *Transufsion*, vol. 16, p. 571 (1976).
Holme, S. et al., "Platelet Storage at 22° C.", *Blood*, vol. 52, p. 425 (1978).
Koerner, K., "Platelet Function After Shipment of Room Temperature Platelet Concentrates", *Vox Sang*, vol. 44, p. 37 (1983).
Heal, J., et al., "Non Centrifugal Plasma Collection Using Cross Flow Membrane Plasmapheresis", *Vox Sang*, vol. 44, p. 156 (1983).
Witbank, T. et al., "Filtration Plasmapheresis In Vivo", *Transfusion*, vol. 21, p. 502 (1981).
Chimel, H., "The Effects of Pressure, Flow Consideration, and Surface Composition on the Filtration Properties of Plasma Filtration Modules", *Plasma Therapy Trans. Tech.*, vol. 4, p. 381 (1983).
Forstrom, R. et al., "Formed Element Deposition onto Filtering Walls", *Trans. Am. Soc. Artif. Int. Organs*, vol. XXI, pp. 602-607 (1975).
Lopez-Leiva, "Ultrafiltration at Low Degrees of Concentration Polarization: Technical Possibilities", pp. 210-651 (Dec. 1980).
Dorson, Int. Appln. WO/82/03567 (Oct. 1982).
English Language Abstracts from Derwent World Patent Index, 1963-1980 (1 page).
Supplementary European Search, Report, European Patent Office, (5 pages).

*Primary Examiner*—Frank Sever
*Attorney, Agent, or Firm*—Paul C. Flattery; Gregory L. Roth; Bradford R. L. Price

[57] ABSTRACT

A reliable flow rate plasmapheresis system includes a rotating enhanced vortex type of membrane filter coupled to receive a flow of anticoagulated whole blood and separate concentrate and filtrate in responses thereto. An anticoagulant pump is coupled to mix controlled amounts of anticoagulant with the input blood flow. Degradation of plasma flow rate during multiple extraction-reinfusion cycles is inhibited by selecting the starging anticoagulant pH value and controlling the anticoagulant flow rate relative to the whole blood to establish a final whole blood/plasma pH value in the range of 6.8 to 7.2, with an anticoagulant to blood ratio in the range of 1:6 to 1:25.

8 Claims, 2 Drawing Sheets

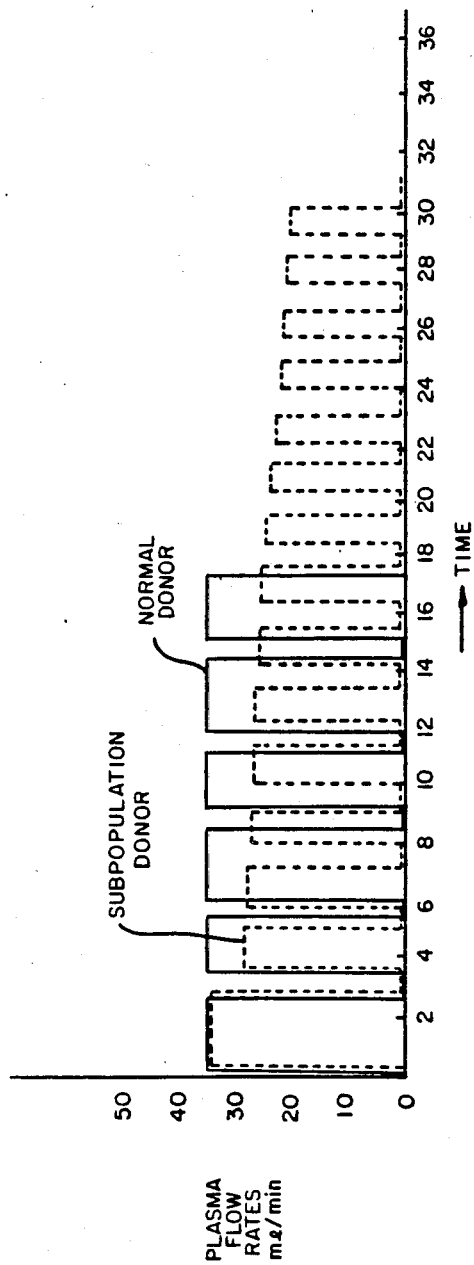

PLASMAPHERESIS SYSTEM AND METHOD

This is a divisional of co-pending application Ser. No. 722,800, filed on Apr. 12, 1985, now U.S. Pat. No. 4,713,176.

BACKGROUND OF THE INVENTION

The use of human blood and blood plasma is so widespread that much work has been directed to blood handling systems, including specifically plasmapheresis systems for extraction of plasma from whole blood. While centrifugation was primarily used in the past in preference to membrane filtration techniques, more recent breakthroughs in membrane filtration technology have occurred that are effecting widespread changes. New plasmapheresis systems are based upon the usage of a vortex enhanced fractionation approach which uses a rotating spinner within a shell, with the surface of the spinner or shell being covered with a filtration membrane. Relative velocities and blood flow conditions are established such that constantly sweeping vortices appear along the length of the spinner to continually present fresh plasma to the surface of the membrane while maintaining high shear conditions. This action enables plasma to be filtered through the membrane without depositing cellular or other matter on the membrane surface so as to increasingly clog the pores of the membrane.

A particular example of this type of system is described in a patent application by Donald W. Schoendorfer entitled "Method And Apparatus For Separation Of Matter From Suspension", Ser. No. 591,925, filed Mar. 21, 1984. With rotating spinner devices of this type, substantially higher plasma flow rates per unit of membrane surface area are obtained than with prior membrane systems, enabling the manufacture of low cost disposable filtration units that can extract two or three units of plasma with minimal donor discomfort and time commitment.

In plasmapheresis systems it is necessary to use an anticoagulant in an amount sufficient to minimize blood clotting but below the level at which adverse physiological effects occur. Automated plasmapheresis systems have typically employed from approximately 10% to approximately 4% of known citrate solutions for restricting clotting tendencies.

In operating plasmapheresis systems using a rotating spinner and vortex action, trauma to the blood is low and it is feasible to utilize anticoagulant at the lower end of the permissible range for most donors. Using a membrane of approximately 60 cm$^3$ in area, plasma "take" rates of 35 ml/min are expected, so that a donor time of approximately 30 minutes is established for about 500 ml of blood. This time interval includes, in a single needle system, periodic dwell periods during which the plasmapheresis system returns packed cells to the donor. During these dwell periods no whole blood flows through the plasmapheresis device and the spinner might not be rotated, so that the blood then in the device is in a static or quasi-static condition. During these dwell periods the blood sometimes reacts with the filter. When this reaction occurs the flow rate through the filter is thereafter significantly reduced. Some flow reduction may also occur during the active periods.

Clinical studies and detailed analysis have shown that this flow reduction occurs with a minor percentage of the donor population, approximately 10%. The difference between this subpopulation of donors and the majority of donors is not fully understood, and the problems appears at this time to pose complex problems that will not be easily resolved. It is not currently known, for example, whether the substandard flow condition arises from a constant donor characteristic or is related to diet, physiological changes or other time variable factors. Thus there is no way to identify specific members of the subpopulation until they have been coupled into the system. It is nonetheless desirable to have an essentially standardized system and clinical procedure for the extraction of plasma from the donor population. It is also a fundamental objective to provide a procedure which gives a substantially constant rate of take of plasma or other constituent.

Extensive investigations as to the functional operation of the filtration process did not reveal the reason for the existence of a special subpopulation. Furthermore, review of the literature as to effects of various levels of anticoagulant were not instructive. Although there have been many investigations of biochemical aspects of the coagulation mechanism, these do not clarify the increase in deposition and consequent lowering of filtration rate in a cyclically operated filtration system. Despite the fact that the effects of fluid characteristics such as pH and ion concentration on blood cells have been extensively studied in a non-shear, storage type environment, the effects in a high shear environment have not been well defined.

SUMMARY OF THE INVENTION

Plasmapheresis systems and methods in accordance with the invention maintain blood in a cyclically operated membrane filtration system in a specifically anticoagulated condition to achieve substantially standardized plasma flow rates for increased percentages of the donor population despite periodic interruptions in the filtration process. The anticoagulant is maintained within a range sufficient to inhibit the onset of blood clotting, without exceeding a ratio recommended by the U.S. Pharmacopea. At the same time, the pH of separated constituent such as anticoagulated whole blood/plasma is held within the range of 6.8 to 7.2, which appears to diminish blood interaction with the filter. It is surmised that it is the action of "activated" platelets with the surface of the membrane which decreases plasma flow. It is a fact that this decrease in plasma flow occurs after the first separation cycle—during the dwell period when packed cells are being returned to the donor. Concurrently with inhibition of clotting, therefore, the platelets are stabilized against changes of physical characteristics and are prevented from agglutination and co-adhesion, which in the minority of the donor population appears to impede plasma flow through the membrane, with a consequent reduction of the plasma flow rate. In a specific example in accordance with the invention, ACD-A anticoagulant having a starting pH of 4.6 is mixed with the whole blood in a ratio of 1:12.5 ACD-A to anticoagulated whole blood. The blood is pumped from a donor into a rotating vortex enhanced type of plasmapheresis system in which vortex flow is maintained. Plasma flow rates for an entire donor population are attained which are equal to or greater than 35 ml/min for the entire extraction cycle.

BRIEF DESCRIPTION OF THE DRAWINGS

A better understanding of the invention may be had by reference to the following description, taken in conjunction with the accompanying drawings, in which:

FIG. 2 is a graphical depiction of plasma flow rates with respect to time in operation of a typical system.

DETAILED DESCRIPTION OF THE INVENTION

Figure 1:
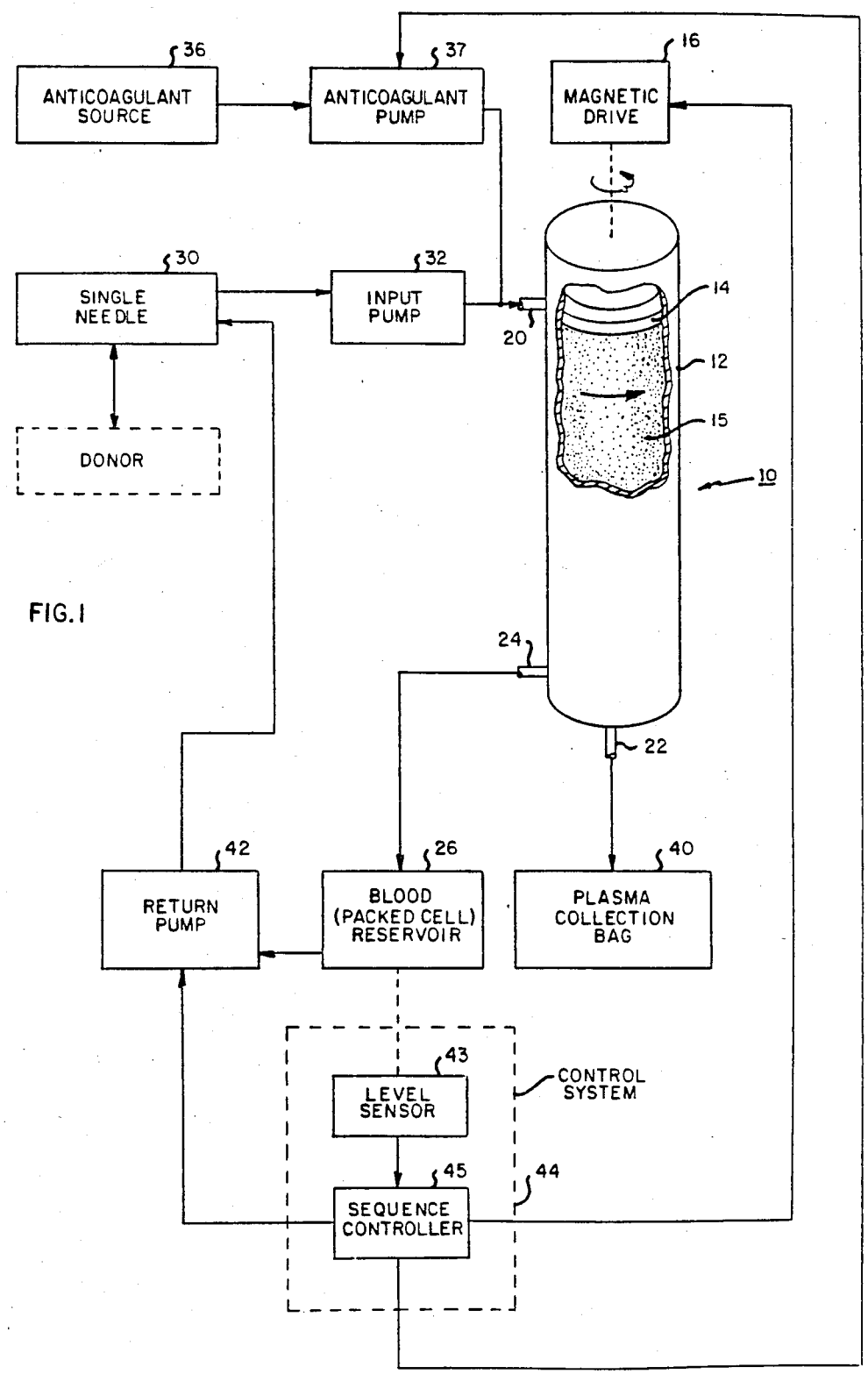
FIG. 1 is a combined block diagram and perspective view of a plasmapheresis system in accordance with the invention.

In a plasmapheresis system and method in accordance with the invention, referring now to FIG. 1, a membrane filtration system 10 comprises a cylindrical body 12 within which a spinner or rotor 14 covered by a membrane 15 is driven remotely, as by a magnetic drive 16, at a selected rotational velocity, here 3600 r.p.m. In the fashion described in the previously referenced Schoendorfer application, whole blood is directed into the space between the rotor 14 and housing 12 from an input port 20. A helical continuity of internally circulating cells is established about the surface of the rotor 14 by virtue of the relationship between rotor diameter, angular velocity, flow gap dimension and blood viscosity. Plasma is continually filtered through the surface of the membrane 15 into channels (not shown) on the surface and in the interior of the rotor 14, from which it passes downwardly, in this instance, to a plasma filtrate outlet port 22. The packed cell remainder fluid is transferred through an outlet port 24 to a reservoir 26, from which it is periodically pumped for return to the donor.

Although a double needle system may be utilized, it is much more typical, for patient comfort, to employ a single needle 30, feeding whole blood from the donor under the impetus of a peristaltic input pump 32 into the inlet port 20. Anticoagulant is concurrently combined with the input whole blood. The anticoagulant is taken from an anticoagulant source 36 at a rate controlled by a separate anticoagulant pump 37. Plasma from the plasma outlet port 22 is fed directly to a plasma collection bag 40, usually simply under gravity flow. To reinfuse packed cells via the single needle, however, a return pump 42 is coupled between the reservoir 26 and the needle 30. A level sensor 43 (a mass sensor may alternatively be used) in a control system 44 (shown only generally) signals a sequence controller 45, such as a microprocessor, when the blood reservoir is full. The full signal activates the return pump 42 during dwell intervals in the plasma extraction cycle. Concurrently, the input pump 32 and anticoagulant pump 37 are stopped and the magnetic drive 16 and rotor 14 are shifted to a lower rotational rate, such as 600 r.p.m. Details of the control system 44 have been omitted for simplicity and brevity inasmuch as they may take many forms including manual on-off actuation of the various pumps.

The proportion of anticoagulant from the source 36 is determined in this system by the anticoagulant pump 37 which is operated to deliver anticoagulant at a selectably controllable rate relative to the whole blood input flow. The plasma collection bag 40 is large enough to receive the entire plasma quantity (e.g. 500 ml of anticoagulated plasma).

Operation of the plasmapheresis system of FIG. 1 presents unique problems because, as seen in FIG. 2, the whole blood which is disposed about the rotor is subjected to alternate conditions of operation. To obtain approximately 500 ml of anticoagulated plasma, a packed cell reservoir 26 of approximately 140 ml is typically used, together with a blood flow rate at approximately 40 hematocrit of 100 ml/min. In the normal donor population, as shown in solid lines in FIG. 2, this results in a filtration cycle of approximately 2½ minutes, with packed cells being delivered to the reservoir 26 at 65 ml/min as 35 ml/min of plasma are delivered to the collection bag 40. For approximately the next two minutes a reinfusion cycle completes the extraction-reinfusion sequence. During the reinfusion cycle the rotor 14 is slowed down to 600 r.p.m. to maintain the vortex condition in the blood about the rotor 14, as the collected packed cells are reinfused in the donor via the return pump 42 and the single needle 30. As indicated by dotted lines in FIG. 2, however, the 10% subpopulation of donors introduces a hitherto unexplained and uncorrectable degradation of performance. After the forced dwell interval, the plasma take is substantially lowered, and thereafter decreases further. This means that the filtration cycles are terminated more quickly because the packed cell concentrate output rate is higher. Consequently, a greater number of cycles, and therefore a greater amount of donor time, are required to collect the desired total amount of plasma.

It is not feasible, according to numerous studies relative to blood collection and storage and donor reaction to anticoagulant to utilize an anticoagulant/blood ratio of >1:6. Furthermore, anticoagulant per se is not a controlling factor in decreased plasma flow, because evidence of coagulation is not observed in the plasma or in the returned packed cells. Evidently the reduced plasma flow is due to some form of deposition at the membrane surface.

The inventors have determined, however, that the changing dynamic conditions of blood flow giving rise to the deposition problem can be fully and effectively counteracted in the great majority of the donor population by the usage of, for example, ACD-A anticoagulant having a pH in the range of 4.5 to 5.5 (preferably 4.4 to 4.8) and in a proportion sufficient to lower the normal blood/plasma pH, typically 7.38, to the range of 6.8 to 7.2. This condition is maintained during all of the filtration cycles, thus carrying over to the dwell cycles in which some whole blood is entrapped between the rotor 14 and the encompassing housing. The ratio of anticoagulant to whole blood is maintained in a range of 1:6 to 1:25 to attain adequate suppression of coagulation while avoiding adverse effects in the donor.

Analysis of the literature for an explanation of this phenomenon has not revealed a basis for full understanding. In the short term handling of platelets in available anticoagulants, for periods of less than approximately 24 hours, no specific anticoagulant expedients have been regarded as necessary to prevent the onset of aggregation of the platelets into larger masses. Thus, inasmuch as the blood is constantly in motion in the present system except during the dwell periods, like reasoning should apply. In longer term storage of platelets than for 24 hours, it has been found beneficial to maintain control of the acidity of the blood constituents so as to be essentially natural, as shown by the following articles:

Murphy, S. and Gardner, F., "Platelet Storage at 22° C.: Role of Gas Transport Across Plastic Containers in Maintenance of Viability", *Blood*, Vol. 46, 209, 1975.

Schlicter, S., "Preservation of Platelet Viability and Function During Storage of Concentrates", *The Blood Platelet Transfusion Therapy*, Alan R. Liss Inc., NY, 83–100, 1978.

Murphy, S. et al, "Storage of Platelets at 22° C.:, *Blood*, Vol. 35, 549, 1970.

Rock, G. And Figuerdo, A., "Metabolic Changes During Platelet Storage", *Transfusion*, Vol. 16, 571, 1976.

Molone, S. et al, "Platelet Storage at 22° C. . . . ", *Blood*, Vol. 52, 425, 1978.

Koerner, K., "Platelet Function After Shipment of Room Temperature Platelet Concentrates", *Vox Sang*, 44, 37, 1983.

Lysaght, M. et al, "Transport Considerations in Flat Sheet Microporous Membrane Plasmapheresis", *Plasma Therapy Transfusion Technology*, 4, 373, 1983.

These disclosures provide a base for conjecture as to the mechanism involved in achieving the desired rate of deposition for virtually all donors using the present plasmapheresis system. As previously indicated, however, there is no understanding at this time of the mechanism which causes the 10% donor subpopulation to interrelate differently with the machine than the majority of donors and no useful test for initially identifying members of the donor subpopulation. It is surmised, however, that the dynamic forces acting on the blood during the initial filtration cycle are substantially different from those acting on the blood during the dwell cycle and that the platelets, although constantly being recirculated in vortices during the relatively short dwell interval, gradually change in characteristics. This change may be expressed as an alteration from normal discoid shape to spherical and even to a pseudopodal, many armed shape having more adherent surface characteristics, but this is thought to be symptomatic of primary causative factors rather than an initiating factor itself. The change is more likely, but still without certainty, due to an imbalance or revised distribution of ionic or other surface charges, whether hydrogen ions alone (pH) or total ions (pK). Whatever the cause, the sequence appears to be reversible on a short term basis by the reintroduction of new pH stabilized whole blood. Consequently, although the initial phases of platelet agglutination may be occurring in the donor subpopulation during and after the first dwell interval, creating a deposit or overlayer of agglutinated platelets on the membrane, stabilization of the ionic balance or other causative factors results in the reversible change, dissolving the deposited structure and enabling a return to the desired filtrate take rate for plasma.

The presence of sufficient anticoagulant in solution in the blood makes available citrate which chelates calcium in the blood and prevents activation of the clotting mechanism. However, the level of anticoagulant must, as previously noted, be limited to no greater than 1:6, and preferably is kept as low as possible (e.g. 1:25) for beneficial return to the donor and minimal dilution of the desired blood product. An advantage of the spinning rotor type of system is that the vortices and flow rates can be substantial but the internal circulation of blood insures that no sharp projections are encountered. Consequently, the blood is not substantially traumatized and tendencies to coagulate are kept low, so that in consequence substantial anticoagulant is not needed.

The incipient tendency toward agglutination on the surface of the filtration membrane, therefore, can be well controlled in this type of system by using an acceptable range (1:6 to 1:25) of anticoagulant, where the anticoagulant has an initially low enough pH range to bring the blood/plasma pH down to the preferred 6.8 to 7.2 range. Clinical tests on hundreds of patients, using ACD-A anticoagulant in a 1:12.5 ratio, have shown a marked decrease in the percentage of donors (from more than about 10% to about 1½%) as to whom the low plasma take problem arises, in comparison to prior conventional anticoagulant formulations. Repeated tests on specific donors whose plasma take falls off with tri-sodium citrate anticoagulant in an acceptable concentration have also demonstrated that normal plasma flux rates are attained in most of the affected donor subpopulation using the procedures of the present invention.

For example, a number of individuals were first identified whose characteristics, given an anticoagulant blood/plasma pH of 7.2 or higher, gave a plasma flow of less than 27 ml/min at the end of the second withdrawal cycle. These individuals were anticoagulated with tri-sodium citrate or ACD-A, had normal hematocrits (44% to 47%) and were giving blood input flow rates of 100 ml/min. Using anticoagulant of sufficient quantity (e.g. 1:10) and sufficiently low starting pH (e.g. 4.6), the plasma flows at the end of the second cycle were in each instance brought into the 36–40 ml/min range.

Whether the onset of agglutination occurs during the filtration interval or during a dwell interval must at this point remain conjectural, but it appears quite clearly that platelet shape changes are reversibly controlled and that tendencies toward buildup or unification of platelet masses are avoided. It is recognized, however, that internal platelet changes may occur during these intervals, and that degranulation, or the emission of internal components of the platelets in the performance of normal functions, may be taking place.

While there have been described above and illustrated in the drawings various forms and modifications of concepts in accordance with the invention, it will be appreciated that the invention is not limited thereto but encompasses all examples and variants within the scope of the appended claims.

What is claimed is:

1. A system for separating plasma filtrate from whole blood comprising:

a filter system including a rotating vortex enhanced separator having a filter membrane, the filter system being coupled to receive a flow of anticoagulated whole blood, a source of anticoaguant fluid having a pH value range of 4.4 to 5.5; and output flows of packed cells and plasma filtrate in response thereto; and the anticoagulant pump coupled to pump an anticoagulant fluid into the flow of whole blood, the pump including means for operating the pump at a rate controlled to provide anticoagulated whole blood with a pH value in the range of 6.8 to 7.2.

2. A system according to claim 1 wherein the filtrate is plasma.

3. A system according to claim 1 wherein the anticoagulant fluid has a pH in the range of 4.5 to 4.8.

4. A system according to claim 1, wherein the blood is subjected to Taylor vortex action adjacent the filter membrane and including means for maintaining the blood flow rates and plasma extraction rates substantially constant during first and subsequent extraction cycles despite variation in donor blood characteristics.

5. A system for filtration of at least one lighter density component from a whole blood flow passing adjacent a filtration membrane comprising:
   a filter membrane;
   a source of anticoagulant fluid having a pH value in the range of 4.4 to 5.5;
   an anticoagulant pump coupled to mix the anticoagulant fluid with the whole blood;
   a blood pump pumping the whole blood with mixed anticoagulant adjacent the filtration membrane for filtering of the lighter density component through the membrane; and
   a control system controlling the anticoagulant pump and the blood pump to maintain the proportion of anticoagulant fluid in the range of 1:6 to 1:25 relative to the whole blood and the pH of the lighter density component filtered from the whole blood in the range of 6.8 to 7.2.

6. A system according to claim 5 wherein the anticoagulant fluid has a pH in the range of 4.5 to 4.8 and the lighter density component is plasma.

7. A system according to claim 6 wherein the control system passes the whole blood mixed with anticoagulant adjacent the membrane in a plurality of cycles with a dwell interval between each cycle.

8. A system according to claim 7 further comprising a housing disposed in spaced relationship to the membrane with the whole blood mixed with anticoagulant passing therebetween and means for rotating the filter membrane to produce Taylor vortices in the space between the housing and the membrane.

* * * * *